US010499664B2

(12) United States Patent
Montoya Kunsting et al.

(10) Patent No.: US 10,499,664 B2
(45) Date of Patent: Dec. 10, 2019

(54) **FISH FEED FORMULATION OF *HYPERICUM PERFORATUM, ROSAMARINUS OFFICIANALIS* OR A MIXTURE THEREOF**

(71) Applicant: UNIVERSIDAD DE SANTIAGO DE CHILE, Santiago (CL)

(72) Inventors: Margarita Paz Montoya Kunsting, Santiago (CL); Marcelo Andrés Cortez San Martin, Santiago (CL); Claudio Antonio Acuña Castillo, Santiago (CL); Sophia Charlotte Mejias Medina, Santiago (CL); Viviana Andrea Ahumada Muñoz, Santiago (CL)

(73) Assignee: Universidad de Santiago de Chile, Santiago (CL)

( * ) Notice: Subject to any disclaimer, the term of this patent is extended or adjusted under 35 U.S.C. 154(b) by 514 days.

(21) Appl. No.: 15/085,590

(22) Filed: Mar. 30, 2016

(65) Prior Publication Data
US 2016/0286834 A1    Oct. 6, 2016

(30) Foreign Application Priority Data

Mar. 31, 2015 (CL) .................................. 796-2015
Dec. 31, 2015 (CL) ................................ 3796-2015

(51) Int. Cl.

| A61K 36/38 | (2006.01) |
| A61K 36/53 | (2006.01) |
| A61K 36/00 | (2006.01) |
| A23K 10/30 | (2016.01) |
| A23K 20/111 | (2016.01) |
| A23K 20/10 | (2016.01) |
| A23K 50/80 | (2016.01) |
| A61K 9/00 | (2006.01) |

(52) U.S. Cl.
CPC .............. *A23K 10/30* (2016.05); *A23K 20/10* (2016.05); *A23K 20/111* (2016.05); *A23K 50/80* (2016.05); *A61K 9/0056* (2013.01); *A61K 36/38* (2013.01); *A61K 36/53* (2013.01)

(58) Field of Classification Search
None
See application file for complete search history.

(56) References Cited

U.S. PATENT DOCUMENTS

| 8,512,766 B2 * | 8/2013 | Brodie | ................ A61K 9/0017 424/725 |
| 2017/0157190 A1 * | 6/2017 | Lamb | ..................... A01N 65/22 |

FOREIGN PATENT DOCUMENTS

| CN | 101024055 A | 8/2007 |
| DE | 199 57 472 A1 | 8/2000 |
| EP | 2 946 672 A1 | 11/2015 |
| WO | 00/59316 A1 | 10/2000 |
| WO | 03/013495 A1 | 2/2003 |
| WO | 2007/090714 A1 | 8/2007 |
| WO | 2008/061757 A1 | 5/2008 |
| WO | 2011/006993 A1 | 1/2011 |

OTHER PUBLICATIONS

European Search Report dated Jul. 25, 2016 for Application No. EP 16 16 3050.
Chilean Office Action dated Dec. 14, 2016 for Application No. CL 201500796.
Chilean Office Action dated Dec. 14, 2016 for Application No. CL 201503796.
espacenet English abstract of CN 101024055 A.
Zilberg, D., et al., "Dried leaves of *Rosmarinus officinalis* as a treatment for streptococcosis in tilapia", Journal of Fish Diseases, vol. 33, No. 4, Apr. 4, 2010, pp. 361-369.
Gultepe, N., et al., Effects of herbs and spice on health status of tilapia (*Oreochromis mossambicus*) challenged with *Streptococcus iniae*, Acta Vet. Brno, vol. 83, No. 2, Jan. 1, 2014, pp. 125-131.
Ostrand, S. L., et al., "Inhibitory Effects of Rosemary Oil on the in Vitro Growth of Six Common Finfish Pathogens", North American Journal of Aquaculture, vol. 74, No. 2, 2012, pp. 230-234.
Barnes, J., et al., "St John's wort (*Hypericum perforatum* L.): a review of its chemistry, pharmacology and clinical properties", Journal of Pharmacy and Pharmacology, vol. 53, No. 5, May 1, 2001, pp. 583-600.

* cited by examiner

*Primary Examiner* — Michael Barker
(74) *Attorney, Agent, or Firm* — Ladas & Parry LLP

(57) ABSTRACT

The present invention thus relates to a formulation comprising St. John's Wort (*Hypericum perforatum*, HP), rosemary (*Rosmarinus officinalis*) extracts or a mixture of both, to improve survival to stressful and pathogens events, and also the feed conversion factor (greater weight gain and growth by delivered food). All of this, without affecting the fish smoltification ability.

1 Claim, 4 Drawing Sheets

FISH FEED FORMULATION OF *HYPERICUM PERFORATUM*, *ROSAMARINUS OFFICIANALIS* OR A MIXTURE THEREOF

FIELD OF THE INVENTION

The present invention relates to the formulation of a foodstuff supplement of a *Hypericum perforatum* (HP), *Rosmarinus officinalis* (RO) extract or a mixture of them, which increases the endogenous antioxidant barriers, increases the weight gain of cultured fish and improves the life span of the cultured fish subject to stressful events and reduces the pathogen infections.

PREVIOUS ART

Intensive fish farming generates a stressful environment that leads to increased susceptibility of fish to infectious diseases, a poor growth rate and high morbidity and mortality of salmons associated with their production process. As from their hatch, fish suffer much stress due to handling processes for their selection, vaccinations, cleaning, medications, transportation, and finally their transfer to the sea (smoltification) to which they are subject. All this causes fish to generate severe stress responses, which are characterized by the release of mediators such as cortisol. This hormone, is capable not only to affect the survival of salmon, but also decreases their immune response, growth and ability to tolerate the seawater. All this finally results in high mortality of fish entering the sea and over the following months. In fact, today obtaining classified smolt, by industry standards as "high quality" is one of the biggest problems of the aquaculture industry. As the fish are not reaching the sea in good or high quality conditions, they are not capable of growing or increasing their size and gaining weight, or surviving in seawater, or they are highly susceptible to infections.

In contrast a fish that reaches the sea in good condition, it is characterized in that it does not have problems of adaptation to the saline media, rapidly beginning to actively eat and having a lower susceptibility to acquiring infectious diseases. Therefore, fish in good conditions at the time of entering the sea, will maintain good sanitary conditions and good production indicators, keeping costs low in the salmon industry. For this reason, there is now a consensus that all pre-smoltification (stage in fish farming) stage is a critical step in the development of the Chilean salmon farming industry. However, the stage in the seawater, it is also highly stressful for the fish, due to the high density of the culturing, high presence of pathogens and high handling (cleaning and medications, mainly). As in the sea there is a high variety and quantity of pathogens, these fish with lower immune capacity, are very vulnerable to disease and death. This low immunity is considered one of the factors which influence the low effectiveness vaccines currently possess. Including the appearance of increasingly aggressive and abundant pathogens, in relation to the reduction of immunity produced by stress.

Moreover, due to stress fish swimming increases, increasing energy expenditure. This causes that food consumed is used in metabolic use, decreasing weight and growth gain. Thus, because this situation increases the amount of fish feed delivered and/or the culture time to achieve proper weights for harvest, this finally reduces the productivity of the industry.

Fish, are also exposed to severe stressing stimulus, such as hypoxia, overcrowding or increasing of the temperature. These conditions can directly generate the death of the fish, causing considerable losses to the industry.

These latter phenomena, such as increased in metabolic rate and stress are also capable of producing oxidative stress in fish. This oxidative stress produces cellular damage, which is believed, corresponds to an important factor in decreasing the response to pathogens and the growth rate. As part of antioxidant barriers, cells have a number of enzymes, among which are: Mn superoxide dismutase (MnSOD), and catalase (CAT). The cells with a high expression of these enzymes have a greater ability of resistance against oxidative events, suffering less damage. That is the reason why, in order to achieve increased endogenous expression of these barriers, may have beneficial and protective effects on the health of the fish.

So far, the efforts in Chile have been focused on improving the culture conditions. There are some initiatives aimed to the creation of facilities designed to reduce the stress on the fish. Additionally, companies producing fish feed; sell special food for the transfer period. Some of these are Golden Immune Transference (Biomar), Spirit smolt (Skretting), Vita transference (Salmochile), containing vitamin C (as an immunostimulant), betaine and/or nucleosides (to help osmoregulation), and some of them add vitamin E and/or astaxanthin (as antioxidant). However, none of these products contain components designed to reduce the stress.

Globally, for handling growth, reproductive, osmoregulators and immune problems, associated with stress in fish, the industry has used fish food which is similar to fish food sold in the country and improve the handling and the culture conditions.

In 2008, Advanced Bionutrition Corp. filed a patent application WO 2009/140327 A2 publication, which is related with salmon feeding when the cultured fish is transferred from fresh water to salt water, so as to improve growth and reduce sensitivity to diseases. This is based on increase of arachidonic acid content in the diet of salmon, during and after the smoltification process (Advanced BioNutrition www.advancedbio-nutrition.com Corp.). However, as its composition consists of special fatty acids, this product has a higher cost in comparison to the formulation proposed in the present patent application.

Stress is a response originated at the central nervous system level, where the brain generates a series of changes, mainly mediated by the release of hormones that allow quick response to a threat. However, when this response of the organism is excessive and is maintained for a longer period of time, an overload is produced, which cause immunosuppression, oxidative stress and even death may be able to occur. The pharmacological management of stress in animals for human consumption is difficult to approach because it is regulated. Thus, the need for products containing components which reduce stress persists in smolts, and in general in fish under breeding. It is for this reason, that the use of plant extracts as a fish food additive, is highly interesting as an alternative for the modulation of the nervous system of the salmon.

The present formulation comprises HP in an amount in the range of 1.5 mg to 15 mg of HP.

The present formulation comprises RO in an amount in the range of 1.5 mg to 15 mg of RO.

DETAILED DESCRIPTION OF THE INVENTION

Figure 1:
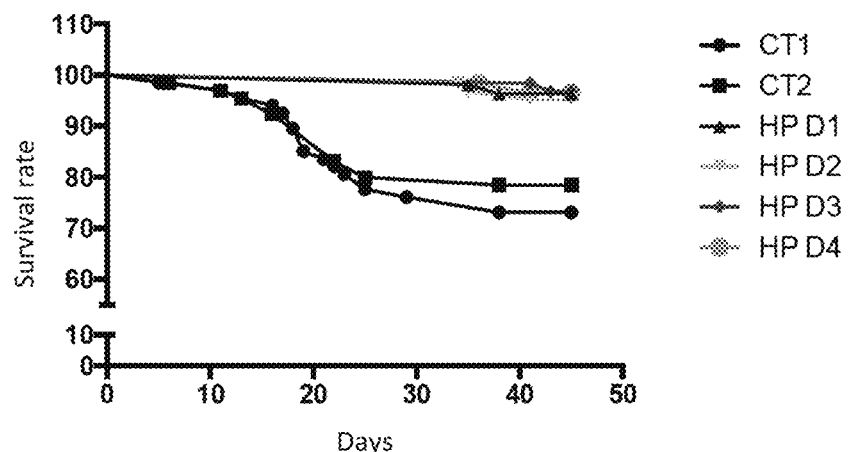
FIG. 1 survival curve of the *S. salar* fish, fed with fish food supplemented with an HP extract, in comparison with the mortality induced by *Yersinia ruckeri*. The effect of the HP consumption on survival period of the *S. salar* compared with the cultures infected with *Yersinia ruckeri*. *Salmo salar* fish cultures, were maintained over a period of 45 days with supplemented feed with an HP extract D1 in doses of (1.8 mg HP/kg fish), D2 (3.5 mg HP/kg fish), D3 (7.0 mg HP/kg fish) or D4 (14 mg HP/kg fish) or control (with food only with fish oil, which is used as impregnating solution).

*Hypericum*, it is a well-known and highly studied plant worldwide, for its modulatory effects of the central nervous system. In this regard, it has been shown to reduce corticotropin (ACTH) levels in rats and humans (Butterweck, V. et. al., Flavonoids of St. John's Wort reduces HPA axis function in rats Medicine plants 2004, 1008. Butterweck, V. et. al. Pharmacological and endocrine effects of *Hypericum perforatum* hypericin and after Repeated treatment. Pharmacopsychiatry 2001 (Suppl.), S2-S7). Said ACTH hormone is released by the hypofisis in response to stress, and it is the main stimulator of the cortisol release. Also, a decrease in cortisol levels in the central nervous system which is the effect of *Hypericum* in rats subjected to stressful stimuli (Franklin M. et. al., has been appreciated. Subchronic treatment with a *Hypericum perforatum* (St John's wort extract) significantly reduces cortisol and corticosterone in the rat's brain. European Neuropsychopharmacology 2004. 7-10). Moreover, studies in rats subject to chronic stress, show that *Hypericum* is able to decrease ACTH, but also improves cellular antioxidant capacity and normalizes immunity mediators (Grundmann O. et. al., Mechanism of St. John's wort extract (STW3-VI) During chronic restraint stress is mediated by the interrelationship of the immune, oxidative defence, and neuroendocrine system. Neuropharmacology 2010 767-773). However, so far it has not been tested using plant extracts to treat fish or aquatic organisms.

The *Rosmarinus officinalis*, is a well-known and widely used plant for its medicinal purposes and for seasoning food in cooking. Considering natural antioxidants, rosemary has been widely accepted as a plant with a very high antioxidant activity. Rosemary, containing phenolic compounds, helps to increase the antioxidant activity of enzymes and reduces the formation of free radicals, creating a possible protection in those etiological diseases where the oxidative stress participates (Afonso et. al., 2013 Phenolic compounds from Rosemary (*Rosmarinus officinalis* L.) attenuate oxidative stress and reduce blood cholesterol in diet-induced Concentrations in hypercholesterolemia rats Nutr Metab (Lond). 10: 19).

In traditional medicine (herbal medicine) rosemary has been used as a stimulant and mild analgesic, and has been considered one of the most effective herbs for treating inflammatory diseases, physical and mental fatigue (Yu M H et. al., Suppression of LPS-induced inflammatory activities by *Rosmarinus officinalis* L. Food Chem 2013; 136: 1047-1054).

A patent (PCT/EP2007/010135) associated with the use of acetone extract rosemary either as medicament, pharmaceutical composition or diet, specifically for the treatment of disorders associated with decreased neurotransmitters, has been issued. The intraperitoneal administration of this extract in adult rats, resulted in a small but significant increase in noradrenaline, but not in the serotonin levels, at the level of central nervous system. By using the Porsolt forced swimming test, widely used for the research for compounds with antidepressant activity, it was observed that oral administration of rosemary extract had significant antidepressant activity in rats. This activity was observed only at higher than 409 mg/kg dose, administered 24, 5 and 1 hour prior to the study. In cell culture, on the other hand, it was found that rosemary extract could inhibit the capture of serotonin, in a dependent way dose. The direct effect of rosemary extract on the activity of the enzyme monoamine oxidase was also analysed A and B (MAO-A and MAO-B), where inhibition dose-dependent manner was also observed. However, none of the examples or tests of this patent, were made on salmonid fish, nor shows effects on protection against pathogens, or weight gain, or increased antioxidant enzymes, or decrease of plasmatic cortisol.

Currently there are a few studies which evaluate the effects of extracts and purified compounds from Rosmarinus officinalis fresh leaves, in aquatic species of commercial value, in order to deliver these benefits to the aquaculture industry. In 2010, Zilberg et. al., showed that the Rosmarinus officinalis extract has direct antimicrobial properties, demonstrating how this herb inhibits the pathogen Streptococcus inae, causing significant economic losses in the culturing of tilapia (Oreochromis sp), without causing resistance treatment of the pathogen. However, this test was performed directly on the bacteria and not its effect is demonstrated to deliver the animal (Zilberg D. et. al 2010. Dried leaves of Rosmarinus officinalis as a treatment for Streptococcosis in tilapia. Journal of Fish Diseases, 33, 361-369). These antibacterial properties, of the essential oil extracted from this plant, have been demonstrated in a broad spectrum of pathogens and researchers attribute these properties to the high content of 1,8-cineole present in the essence. In all these cases, the tests have been carried out directly made on pathogens and no protection assays are used on animals (Viuda-Martos, M. et. al., 2008. Antibacterial activity of different essential oils obtained from different plants widely used spices in the Mediterranean diet. International Journal of Food Science and Technology, 43, 526-531).

Another property studied is their use as hepatoprotective, based on its composition which is rich in rosmarinic acid (Raskovic A. et. al., Antioxidant activity of rosemary (Rosmarinus officinalis L.) essential oil and Its hepatoprotective BMC Complement Altern Med potential 2014; 14: 225.). In this regard there is a study of year 2015 where the administration of rosemary extract to the Sparus aurata species, showed a sharp decrease in hepatic steatosis and a reduction in the plasmatic glucose levels and triglycerides. This suggests that the addition of rosemary to the diet reduces the imbalance in metabolism caused by ad libitum feeding of diets rich in fats and intensive aquaculture conditions and also improves liver functions, as for the liver is responsible for the homeostasis of glucose and triglycerides in the blood. This effect could offset the weakness in the physiology of the liver produced by imbalanced by its high percentage of oils (Hernandez A. et. al., 2015. Preliminary insights into the incorporation of rosemary extract diets (Rosmarinus officinalis L.) in fish food: influence on performance and physiology gilthead sea bream of (Sparus aurata) Fish Physiol Biochem. 41 (4): 1065-1074).

The present invention differs from this study because it does not propose the use as hepatoprotective. The invention provides the aquaculture industry, improvements in survival of the cultured fish which are under in intensive cultivation processes which are challenged by common pathogens, an increase of endogenous antioxidants fish barriers, reduction of the stress and an improvement in growth. Additionally, the comments of the results, it was found that low doses of rosemary extract per kg of fish (1.8 mg/kg fish), unlike the previous study, where use is made of an optimal dose of 600 mg/kg of fish.

Another beneficial property of rosemary is its anti-inflammatory capacity. Mengoni in year 2011 shows that a pretreatment with anti-inflammatory compound of rosemary, such as carnosic acid (CA) and carnosol (CS), in inflamed mouse ears, differentially regulate gene expression associated with inflammation, such as IL-1β and TNF-α (reducing their expression) and selectively inhibiting COX-2 but not COX-1, demonstrating the pharmacological basis for anti-inflammatory properties reported for CA and CS. (Mengoni E S et. al., 2011. Suppression of COX-2, IL-1β and TNF-α expression and leukocyte infiltration in inflamed skin by bioactive compounds from Rosmarinus officinalis L. Herbal Medicine 82 (3): 414-21)

In 2012, the University of Murcia along with IMIDA and Nutrafur SA, presented the patent application P201230114 (ES 2421315 A1), which refers to the use of a rosemary plant extract and its utilization as a supplement, in the elaboration of feedstock for animal feed (ruminants). The meat coming from supplemented feed animals with rosemary extract, has a greater antimicrobial and antioxidant capacity than the meat of animals fed with unsupplemented feed, so the extract improves quality and increases its commercial life.

However, this study only considers quality benefits of ruminant meat to be commercialized.

Several works have also used rosemary extract or rosemary oil as a replacement for commonly used antioxidants in the diet of coho salmon or rainbow trout and analysing the effect on salmon fresh meat after storage at $-0.4°$ F. ($-18°$ C.). These works, sought to demonstrate the effectiveness of rosemary extract as a preservative in salmon meat as a natural replacement for synthetic antioxidants currently used in the salmon diets. These exogenous antioxidants used in the diet have been observed that go directly to the meat, where they would exert its antioxidant effect.

The proposal solution in this application is the implementation of a low-cost therapy aimed to managing the salmonid stress and allows a widespread use during the production process. Specifically, the use of known plant extracts for their antioxidant and modulatory ability of the nervous system is proposed, as is the St. John's Wort (Hypericum perforatum, HP). Thus, the negative effects of high levels of physiological stress (death of animals, immunosuppression and oxidative stress) are reduced.

The present invention also suggests that rosemary extract is capable of improving the antioxidant enzymes endogenous expression (catalase and superoxide dismutase) in the fish, which would generate increased resistance to oxidative stress caused by highly stressful processes like smoltification, transportation, vaccination, overcrowding, among others, that recurrently occur during development and large-scale production of the aquaculture industry. None of the above documents discloses a rosemary extract that is able to enhance the antioxidant enzymes expression (catalase and superoxide dismutase) in the fish, which would generate greater resistance to oxidative stress caused by highly stressful processes such as smoltification, transport, vaccinations, overcrowding, among others, that recurrently occur during development and large-scale production of the aquaculture industry. This means that the present invention solves the problem of intensive fish farming stress, or aquaculture industrial crops, from freshwater ponds to its cultivation in sea water, which means lower mortality.

Currently, in salmon are developing a series of preventive and curative treatments, including immunostimulants, supplements with antioxidant activity, anti-virals and vaccines. However, none of these approaches aims to manage stress as the source of the problem.

The present invention thus relates to a formulation comprising St. John's Wort (*Hypericum perforatum*, HP), rosemary (*Rosmarinus officinalis*) extracts or a mixture of both, to improve survival to stressful and pathogens events, and also the feed conversion factor (greater weight gain and growth by delivered food). All of this, without affecting the fish smoltification ability.

The present supplement feed formulation comprising St. John's Wort extract, rosemary or a mixture of both, in amounts of 1.5 mg/kg fish to 15 mg/kg fish, as is supported by the following embodiments only disclosed as an example:

EXAMPLE 1

Analysis of Survival Against St. John's Wort Extract Pathogen.

*Salmo salar* pre-smolts from 60 to 80 g were purchased and transported from aquaculture. 60 fish were placed in each experimental tank. Fish began to consume food with an HP extract supplemented (D1 dose (1.8 mg HP/kg fish), D2 (3.5 mg HP/kg fish), D3 (7.0 mg HP/kg fish), D4 (14 mg HP/kg fish). Five days later, the fish began with an outbreak of "red mouth" disease (produced by *Yersinia ruckeri*), which was confirmed by specific analysis. The fish continued throughout the outbreak with feed supplemented with HP extracts in 4 doses previously indicated. On day 45, the deaths of the fish stopped and samples were taken from them. As shown in FIG. 1, during the *Yersinia* outbreak, fish from 2 control groups (black) had mortality about 20 to 30% (14 and 18 dead fish in control ponds). However, fish that were maintained with food supplemented with an HP extract in 4 doses, showed a mortality that did not exceed 5% (deaths of between 2 and 3 fish in the period). This protection was observed at all tested doses with a RSP (relative survival rate) of 89.

EXAMPLE 2

Growth Effect Analysis (Weight and Height) and Feed Conversion Factor (FCF) of St. John's Wort Extract.

30 *Salmo salar* fish 60 to 80 g were fed 1% BW (body weight) for 21 days. The feed was supplemented with an HP dose of 7 mg HP/kg fish, plus supplemented control only with the 2% impregnating solution. In Table 1, the average difference between the weight at the beginning and end of the supply supplementing food with HP extract, and Feed Conversion Factor (FCF) is shown. The FCF is the measure of how many kg of food are required to produce 1 kg of salmon. It is therefore a widely used indicator in industry.

FCF, presents a hyperbolic behaviour regarding to the delivered food, so that high values can represent overfeeding (no growth) or undernourishment. Overall, a good FCF should be about 1.1 and 1.2. As shown in Table 1, the fish without supplemented feed gain 2.3 g in the period, with an FCF of 6.7, confirming the low amount of feed delivered (undernourishment). Interestingly, fish fed with supplemented food with an HP extract, showed a weight gain of 6.8 g with an FCF of 2.2, which although is not optimal, is much closer to the desirable.

In the analysis of the fish size, it was observed that control fish gained an average of 0.15" (0.4 cm) in size, while those fed with HP20, fish did in 0.31" (0.8 cm).

TABLE 1

Summary of average weight gain, height gain and feed conversion factor of 20 fish during a period of 21 days of 1.0% feeding of their body weight, using feed supplemented with an HP extract dose D3 (7.0 mg HP/kg fish) or control

| Condition | Average weight gain in 21 days (g) | Average height gain in 21 days (cm) | Feed (FCF) conversion factor |
|---|---|---|---|
| Control | 2.3 | 0.4 | 6.7 |
| HP D3 | 6.8 | 0.8 | 2.2 |

EXAMPLE 3

Analysis of Growth Effect (Weight and Height) and Feed Conversion Factor (FCF) with RO Extract.

30 *Salmo salar* fish from 60 to 80 g were fed 1% BW (body weight) for 21 days. The feed was supplemented with an RO dose of 7 mg RO/kg fish, plus supplemented control only with the 2% impregnating solution. In Table 1, the average difference between the weight at the beginning and end of the supply supplementing food with RO extract, and feed conversion factor (FCF) is shown.

The FCF is the measure of how many kg of food is needed to produce 1 kg of salmon. It is therefore a widely used indicator in industry. FCF presents a hyperbolic behaviour regarding the delivered food, so that high values can represent overfeeding (no growth) or nourishment. In general, a good FCF should be around 1.1 and 1.2. As shown in Table 2, without fish feed supplemented gain 2.3 g in the period, with an FCF of 6.7, confirming the low amount of feed delivered (nourishment). Interestingly, fish fed with supplemented food with an RO extract showed a weight gain of 8.9 g with an FCF of 1.7, which although is not optimal, is much closer to the desirable despite being nourishment.

In the size analysis of the fish, it was observed that control fish gained an average of 0.15" (0.4 cm) in size, while those fish fed with RO D3, and did in 0.354" (0.9 cm).

TABLE 2

Summary of average weight gain, height gain and feed conversion factor of 20 fish over a period of 21 days of 1.0% feeding of their body weight, using feed supplemented with an RO extract D3 (7.0 mg RO/kg fish) or control

| Condition | Average weight gain in 21 days (g) | Average height gain in 21 days (cm) | Feed (FCF) conversion factor |
|---|---|---|---|
| Control | 2.3 | 0.4 | 6.7 |
| RO D3 | 8.9 | 0.9 | 1.7 |

EXAMPLE 4

Analysis of Plasma Cortisol Levels with HP Extract.

Figure 3:
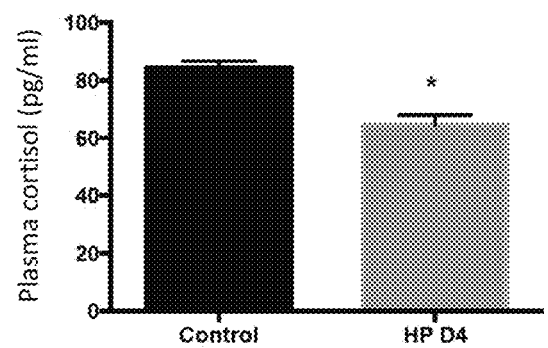
FIG. 3 Determination of plasmatic cortisol in fish fed with supplemented food with an HP extract. *Salmo salar* fish, were maintained over a period of 45 days with supplemented feed with an HP extract, D4 dose (14 mg HP/kg fish) or control (with food only with impregnating solution).

It was examined whether the fish that consumed supplemented feed with an HP extract decreased the basal cortisol levels, which is one of the major stress mediators and it can cause a decline in immunity. Pre-smolt, fish were fed for 45 days with supplemented feed with an HP extract from, HP 14 mg/kg fish. As shown in FIG. 3, the fish that consumed HP showed a statistically significant decrease of circulating cortisol levels. This could positively impact in the fish, reducing the adverse chronic effects presented by this hormone, particularly in immunity. However, levels remained high which is desirable, since cortisol it is also an important hormone for the smoltification physiological adaptation.

EXAMPLE 5

Analysis of Plasma Cortisol Levels with RO Extract.

Figure 2:
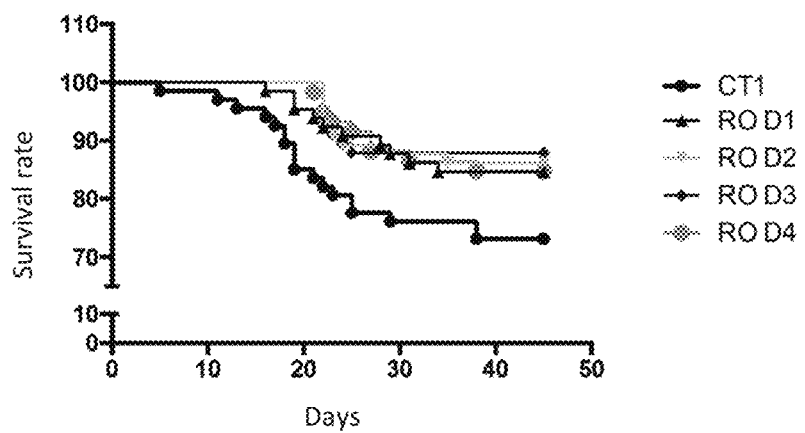
FIG. 2 survival curve of *S. salar* with supplemented food with an RO extract, against the culture mortality induced by *Yersinia ruckeri*. Effect of the RO consumption on survival of *S. salar* against *Yersinia ruckeri* infection. *Salmo salar* fish cultures, were maintained over a period of 45 days with supplemented feed with an RO extract D1 dose (1.8 mg RO/kg fish), D2 (3.5 mg RO/kg fish), D3 (7.0 mg RO/kg fish) or D4 (14 mg RO/kg fish) or control (with food only with fish oil, which is used as impregnating solution).

It was analysed whether consuming supplemented feed with an RO extract fish, decreased basal cortisol levels, which is one of the major stress mediators and can cause decline in the immunity. Pre-smolt, fish were fed for 45 days with feed supplemented with an RO extract; D1 dose (1.8 mg RO/kg fish) and D4 dose (14 mg RO/kg fish). As shown in FIG. 2, the fish consumed RO showed statistically significant decreased levels of circulating cortisol in both doses. This could positively impact in the fish, reducing the adverse chronic effects presented by this hormone, particularly in immunity. However, levels remained high, which is desirable since cortisol it is also an important hormone to the smoltification physiological adaptation.

EXAMPLE 6

Analysis of the Pump Activity of Gill Na+/K+ ATPase with HP Extract.

To analyse whether the consumption of supplemented feed with an HP extract could interfere with the smoltification ability of the fish, the pumps activity of the gill Na+/K+ATPase in the fish with supplemented feed was measured with an HP extract of dose D1 (HP 1.8 mg/kg fish), D2 (3.5 mg HP/kg fish), D3 (7.0 mg HP/kg fish) or D4 (HP 14 mg/kg fish) for 45 days. Gill samples were taken and was determined the pumps activity.

As can be seen in Table 3, no significant differences in the pumps activity gill Na+/K+ATPase between control fish and fish with supplemented feed, at any of the used doses. This activity would indicate that the fish preserve the ability to maintain plasma osmolality and survive in seawater. In fact, the fish showed no mortality during the first 48 hours of its passage to seawater.

TABLE 3

Summary of average pumps activity gill Na+/K+ ATPase in fish kept for a period of 45 days supplemented feed with an HP extract (D1 dose (1.8 mg HP/kg fish), D2 (3.5 HP mg/kg fish), D3 (7.0 mg HP/kg fish) or D4 (14 mg HP/kg fish)) or control (with food only with impregnating solution).

| Condition | Gill Na+/K+ ATPase activity (U/mg) |
|---|---|
| Control | 13.33 ± 0.67 |
| HPD1 | 13.36 ± 0.50 |
| HPD2 | 13.48 ± 0.50 |
| HPD3 | 13.04 ± 0.36 |
| HPD4 | 13.08 ± 0.59 |

EXAMPLE 7

Analysis of the Pumps Activity of the Gill Na+/K+ ATPase with RO Extract.

To analyse whether the consumption of supplemented feed with an RO extract could interfere with the smoltification ability of fish, the pumps activity of the gill Na+/K+ ATPase of fish with supplemented feed was measured with an HP extract dose D1 (1.8 mg RO/kg fish), D2 (3.5 mg RO/kg fish), D3 (7.0 mg RO/kg fish) or D4 (14 mg RO/kg fish) for 45 days. Gill samples were taken and the pumps activity was determined.

As can be seen in Table 4, no significant differences in the pumps activity of the gill Na+/K+ATPase between control fish and fish feed supplemented with, any of the used doses. This activity would indicate that the fish preserve the ability to maintain plasma osmolality and survive in seawater. In fact, the fish showed no mortality during the first 48 hours of its passage to seawater.

TABLE 4

Summary of average activity pumps gill Na+/K+ ATPase fish kept for a period of 45 days feed supplemented with an HP extract (D1 dose (1.8 mg RO/kg fish), D2 (3.5 mg RO/kg fish), D3 (7.0 mg RO/kg fish) or D4 (14 mg RO/kg fish)) or control (with only food with impregnating solution).

| Condition | Gill Na+/K+ ATPase activity (U/mg) |
|---|---|
| Control | 13.33 ± 0.67 |
| ROD1 | 13.52 ± 0.30 |
| ROD2 | 13.26 ± 0.55 |
| ROD3 | 12.82 ± 0.82 |
| ROD4 | 13.12 ± 0.43 |

EXAMPLE 8

Analysis of Mortality Versus Highly Stressful Events with HP and RO Extract Mixture.

Figure 5:
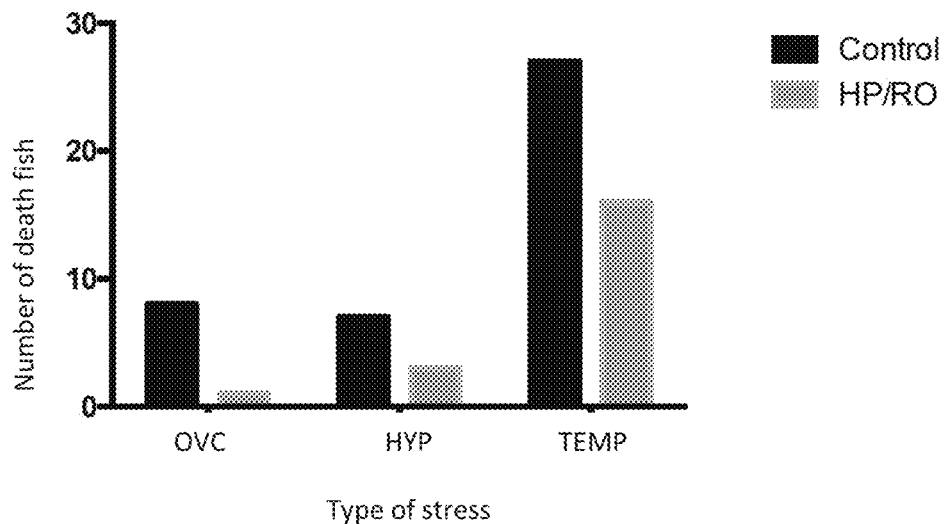
FIG. 5 Determination of plasmatic cortisol in fish fed with supplemented food with an HP extract. *Salmo salar* fish were placed in experimentation ponds and were subjected to various stressful stimuli. OVC corresponds to overcrowding (150 kg/m$^3$) for 24 h. HYP corresponds to hypoxia, where the aeration system was disconnected, until saturation fell to about 32%, and then the aeration of the pond was resumed. TEMP corresponds to the temperature rise, reaching 24° C. during 24 h. Ten minutes before initiating each stimulation, 90 mg HP extract and 90 mg of *Rosmarinus officinalis* (RO) extract were dissolved in the experimentation pond (which had a volume 150 L). The number of dead fish was controlled over a period of 48 hours after the stress conditions were initiated.

For this analysis, they were placed 60 pre-smolts *S. salar* between 60 to 80 g in an experimental pond. Prior to the start of the test, 90 mg of HP extract and 90 mg of RO extract called (*Rosmarinus officinalis*) dissolved in pond water (150 L) they were placed and proceeded to stressful stimuli. These were: overcrowding by 24 h (OVC), hypoxia (HYP) and increase in temperature for 24 h (TEMP). As seen in FIG. 5, with all stimuli used, there was a smaller amount of death during the first 48 hours of stress starting. In the case of overcrowding, fish that had no extract in water they presented 9 dead, while in the pond with extracts only was produced 1 death. For hypoxia, 8 deaths occurred in the control (with food only with impregnating solution (fish oil), no extracts), whereas in the presence of HP extract only 3. In the case of temperature in control (with food only with impregnating solution, without extracts) 27 fish died in the presence of the extracts were 17 dead.

EXAMPLE 9

Expression Analysis of Mn Superoxide Dismutase (Mn-SOD) in Fish Treated with RO or Controls.

Figure 6:
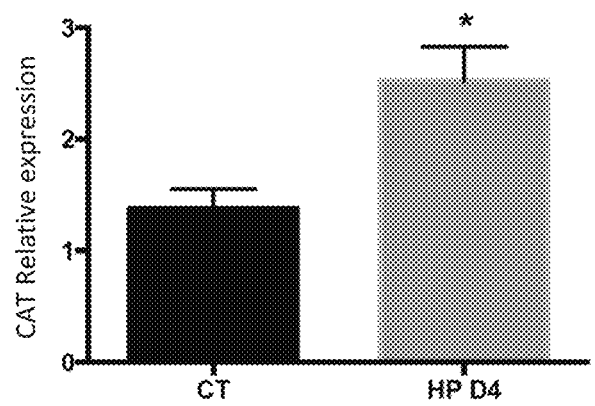
FIG. 6 Determination of relative catalase expression (CAT) in the liver of cultured fish which had been fed with supplemented food with an HP extract. *Salmo salar* fish, were maintained over a period of 45 days with supplemented feed with an HP extract dose D4 (14 mg HP/kg fish) or controlled (with food only with impregnating solution). For the analysis, the measurement of the CAT expression was performed using Real Time PCR, which had been normalized with reference to the rRNA18S expression as constitutive expression gene. (*p<0.05. Kruskal-Wallis Test).
Figure 7:
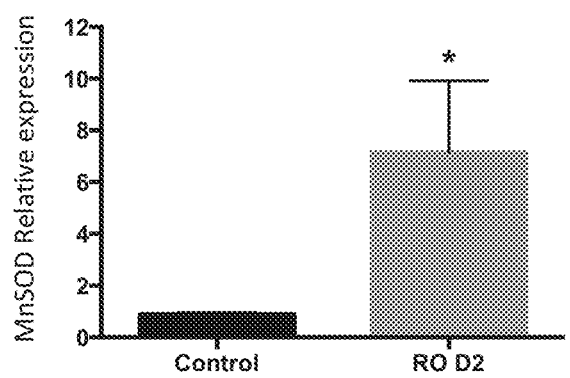
FIG. 7 Determination of relative Mn dismutase superoxide (MnSOD) expression in the liver of fish cultures fed with supplemented food with an RO extract. *Salmo salar* fish, were maintained over a period of 45 days with supplemented feed with an extract of RO dose D2 (3.5 mg RO/kg fish) or control (with only food with impregnating solution). For analysis, the measurement of the expression of MnSOD was performed using Real Time PCR, normalized for the expression of rRNA18S as constitutive expression gene. (*p<0.05. Kruskal-Wallis Test).
Figure 8:
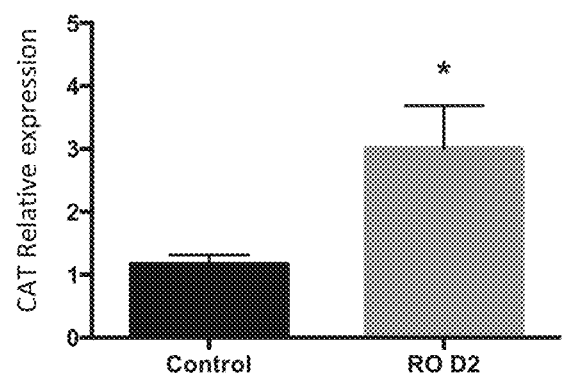
FIG. 8 Determination of relative catalase expression (CAT) in the liver of fish fed with supplemented food with an RO extract. *Salmo salar* fish, were maintained over a period of 45 days with supplemented feed with an RO extract dose D2 (3.5 mg RO/kg fish) or control (with only food with impregnating solution). For analysis, measurement of the expression of CAT was performed using Real Time PCR, being normalized for the expression of rRNA18S as constitutive expression gene. (*p<0.05. Kruskal-Wallis Test).

In order to analyse, if the consumption of food supplemented with an RO extract could enhance endogenous antioxidant barriers, the expression of MnSOD enzyme in the liver of *S. salar* who consumed the extract was analysed. Pre-smolt, fish were fed for 45 days with supplemented feed with an RO extract, dose D2 3.5 mg RO/kg fish. As shown in FIG. 6, the fish consumed supplemented food with an RO extract showed an average increase of about 7 times MnSOD expression in liver. This means that the treated fish have a higher ability to respond against oxidative stress, than non-supplementing food consumed RO extract.

EXAMPLE 10

Analysis of the Catalase Expression in Fish Treated with HP or Controls.

In order to analyse, if the supplemented food consumption with an HP extract could enhance endogenous antioxidant barriers, the catalase expression in *S. salar* liver who consumed the extract was studied. Pre-smolt, fish were fed for 45 days with supplemented feed with an HP extract, 14 mg HP/kg fish. As shown in FIG. 6, the fish consuming supplemented feed with an HP extract, showed a statistically significant increase in liver catalase expression. This means that the treated fish have a greater ability to respond against oxidative stress than those who did not consume supplemented feed with an HP extract.

EXAMPLE 11

Analysis of Catalase Expression in Fish Treated with RO or Controls.

Figure 4:
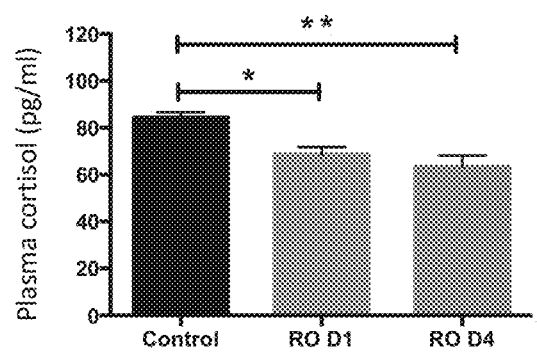
FIG. 4 Determination of plasmatic cortisol in fish fed with supplemented food with an RO extract. *Salmo salar* Fish, were maintained over a period of 45 days with supplemented feed with an RO extract, D1 dose (1.8 mg RO/kg fish) and D4 (14 mg RO/kg fish) or control (only with food impregnating solution) (*p<0.05;**p<0.01 Tuckey multiple comparison tests).

In order to analyse, if the consumption of supplemented food with an RO extract could enhance other enzymes belonging to endogenous antioxidants barriers, the catalase expression in *S. salar* liver, who consumed this extract was analysed. Pre-smolt, fish were fed for 45 days with supplemented feed with an RO extract of dose D2 3.5 mg HP/Kg fish. As shown in FIG. 4, the fish consumed supplemented food with an RO extract showed an average gain of slightly more than 3 times, in the MnSOD expression in liver. This means that the treated fish have a higher ability to respond against oxidative stress, than those without consumed supplemented food with an RO extract.

The invention claimed is:

1. Method of enhancing gain in weight of cultured fish which comprises administering to said fish a formulation comprising St. John's Wort (*Hypericum perforatum*) extract, *Rosmarinus officinalis* (RO) extract or a mixture of both in an amount of from 1.5 mg/kg of fish to 15 mg/kg of fish for a period sufficient to enhance the weight gain of the fish.

* * * * *